United States Patent
Smythe et al.

(10) Patent No.: US 7,429,920 B2
(45) Date of Patent: Sep. 30, 2008

(54) RADIO FREQUENCY IDENTIFICATION AND TAGGING FOR IMPLANTABLE MEDICAL DEVICES AND MEDICAL DEVICE SYSTEMS

(75) Inventors: Alan H. Smythe, White Bear Lake, MN (US); Howard D. Simms, Jr., Shoreview, MN (US); Kenneth P. Hoyme, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 226 days.

(21) Appl. No.: 11/185,263

(22) Filed: Jul. 20, 2005

(65) Prior Publication Data

US 2007/0018810 A1 Jan. 25, 2007

(51) Int. Cl.
*G08B 13/14* (2006.01)
*A61B 5/00* (2006.01)
*A61B 5/05* (2006.01)

(52) U.S. Cl. ............... 340/539.12; 340/572.3; 600/423; 600/325; 600/327; 600/333

(58) Field of Classification Search ............ 340/539.12, 340/568.1–572.9; 600/333, 325, 327, 332, 600/339, 423, 424, 446, 38–41; 128/843
See application file for complete search history.

(56) References Cited

U.S. PATENT DOCUMENTS

| | | | | |
|---|---|---|---|---|
| 4,658,818 | A * | 4/1987 | Miller et al. | 606/1 |
| 5,626,630 | A * | 5/1997 | Markowitz et al. | 607/60 |
| 2004/0031626 | A1* | 2/2004 | Morris et al. | 177/25.17 |
| 2005/0010300 | A1* | 1/2005 | Disilvestro et al. | 623/18.12 |
| 2005/0012617 | A1* | 1/2005 | DiSilvestro et al. | 340/572.8 |
| 2005/0212675 | A1* | 9/2005 | Green | 340/572.8 |
| 2005/0247319 | A1* | 11/2005 | Berger | 128/898 |
| 2005/0258242 | A1 | 11/2005 | Zarembo | |
| 2006/0145871 | A1* | 7/2006 | Donati et al. | 340/572.8 |
| 2006/0173291 | A1* | 8/2006 | Glossop | 600/424 |
| 2006/0184396 | A1* | 8/2006 | Dennis et al. | 705/4 |

* cited by examiner

*Primary Examiner*—George A Bugg
*Assistant Examiner*—Jennifer Mehmood
(74) *Attorney, Agent, or Firm*—Schwegman, Lundberg & Woessner, P.A.

(57) ABSTRACT

Systems and methods for radio frequency identification and tagging of implantable medical devices and their components are disclosed. A preferred embodiment includes tagging a device and its components with manufacturing information relating to the device and it components and with information identifying a patient using the device. The information can be automatically transmitted or extracted from the device when the device or its components come into communication range of an external programmer or other device adapted to read or sense the RFID information. Some embodiments of a system disclosed herein can also be configured as a component of an Advanced Patient Management System that helps better monitor, predict and manage chronic diseases.

24 Claims, 2 Drawing Sheets

RADIO FREQUENCY IDENTIFICATION AND TAGGING FOR IMPLANTABLE MEDICAL DEVICES AND MEDICAL DEVICE SYSTEMS

TECHNICAL FIELD

The present systems and methods relate generally to implantable medical devices and particularly, but not by way of limitation, to such a system that provides for radio frequency identification and tagging of the components of such devices and the identification of patients using such devices.

BACKGROUND

Tagging and tracking of products and devices utilizing radio frequency identification ("RFID") is widely used in manufacturing and packaging processes, but has not been used to label implantable medical devices.

As described by the Association for Automatic Identification and Mobility of Warrendale, Pa. ("AIM"), a basic RFID system consists of three components: an antenna or coil; a transceiver (with decoder); and a transponder (RF tag) electronically programmed with unique information. The electromagnetic field produced by the antenna can be constantly present when multiple tags are expected continually. If constant interrogation is not required, the field can be activated by a sensor device.

Often the antenna is packaged with the transceiver and decoder to become a reader or interrogator, which can be configured either as a handheld or a fixed-mount device. The reader emits radio waves in ranges of anywhere from one inch to 100 feet or more, depending upon its power output and the radio frequency used. When a RFID tag passes through the electromagnetic zone, it detects the reader's activation signal. The reader decodes the data encoded in the tag's integrated circuit (typically a silicon chip) and the data is passed to the host computer for processing.

AIM further describes RFID tags as available in a wide variety of shapes and sizes. Tags can be as small as a pencil lead in diameter and one-half inch in length. Thus, an RFID tag of this size is suitable as a component of an implantable medical device.

According to AIM, RFID tags are categorized as either active or passive. Active RFID tags are powered by an internal battery and are typically read/write, i.e., tag data can be rewritten and/or modified. An active tag's memory size varies according to application requirements; some systems operate with up to 1 MB of memory. In a typical read/write RFID work-in-process system, a tag might give a machine a set of instructions, and the machine would then report its performance to the tag. This encoded data would then become part of the tagged part's history. The battery-supplied power of an active tag generally gives it a longer read range. The trade off is greater size, greater cost, and an operational life limited to about 10 years depending on operating temperatures and battery type. However, such an operational lifespan is well suited for an active tag included with an implantable medical device.

Passive RFID tags operate without an internal power source and obtain operating power that is generated by the reader. Consequently, passive tags are much lighter than active tags, less expensive, and offer a virtually unlimited operational lifetime. The trade off is that they have shorter read ranges than active tags and require a higher-powered reader. Read-only tags are typically passive and are programmed with a unique set of data (usually 32 to 128 bits) that cannot be modified.

AIM reports that the significant advantage of all types of RFID systems is the non-contact, non-line-of-sight nature of the technology. Tags can be read through a variety of substances, including human tissue, where barcodes or other, traditional optically read technologies would be useless. RFID tags can also be read in challenging circumstances at remarkable speeds, in most cases responding in less than 100 milliseconds. The read/write capability of an active RFID system is also a significant advantage in interactive applications such as work-in-process or product tracking.

Although RFID is a costlier technology (compared to barcode systems), it has become indispensable for a wide range of automated data collection and identification applications that would not be possible otherwise.

Current medical device configurations for implanted pulse generators, such as pacemakers or defibrillators, store ID's in a microprocessor memory and use custom communication protocols in an external programmer to extract the information. To accomplish their therapeutic purpose, such devices deliver timed sequences of low energy electrical stimuli, called pace pulses, to the heart. Such stimuli are delivered via an intravascular lead wire or catheter (referred to as a "lead") having one or more electrodes disposed in or about the heart.

However, pulse generators with extractable identification information may not identify the manufacturer or type of the lead that is connected to the implantable medical device ("IMD") in the case where the lead has been replaced in a patient. In addition, a custom communication protocol may not be compatible with components from different manufacturers. It is often the case that an original pulse generator lead, for example, is replaced with a lead from a different manufacturer. So, even if the manufacturer's pulse generator could identify the original manufacturer's lead, the manufacturer's custom communication protocol would typically fail to recognize the replacement lead. However, if IMD manufacturers adopt an industry-wide communication protocol, that would solve the problem of component identification and allow for confident interchangeability of component parts. There is a need for an industry-wide communications protocol that allows for IMD and associated implanted component identification. Such a communications protocol would provide IMD and associated implanted component manufactures confidence in using IMD associated components interchangeably.

Devices such as leads and stents do not currently have an electronic mechanism for identification of their model/serial number, and manufacturing information. Most often, X-rays are the most common approach to identifying such devices. In addition, leads and stents typically do not have their own power sources. There is a need for leads, stents and other IMD components to have electronic mechanisms for identification. Such identification mechanisms would simplify the identification of a particular model or associated serial number of such devices along with other specific information about the device and/or its component parts.

Leads, stents and other IMD components that have electronic mechanisms for identification would be used in combination with IMDs and a system that provides for identification and tagging of specific medical devices and the identification of patients using such devices to automatically and quickly identify manufacturing information about the devices, their component parts and the recipients of such devices. Such a system will improve the manufacturer's and the clinician's ability to manage and monitor the devices while in clinical use.

SUMMARY

According to one aspect of the invention, there is provided a medical device system comprising a plurality of radio frequency identification tags that include information specific to a plurality of components of the system and at least one patient. The system further includes an identification module adapted to identify each of the plurality of radio frequency identification tags and an automatic communications module adapted to convey the identified RFID tag to a clinician or other authorized recipient. As used herein, a "clinician" can be a physician, physician assistant (PA), nurse, medical technologist, or any other patient health care provider. With the identification of each of the plurality of radio frequency identification tags, a clinician may be advised of the specifics of each individual component involved in a configured implanted system comprised of implanted medical devices and associated implanted components.

The components of the system may include, by way of non-limiting example only, a pulse generator, i.e., a pacemaker or defibrillator, a lead of a pulse generator or a stent. Those of skill in the art will recognize that other implantable medical devices are suitable for RF tagging to identify the device's manufacturing information and/or its user.

The identification module may be integrated with the implantable medical device or not. By way of non-limiting example only, a pacemaker or defibrillator may include an integrated identification module that automatically identifies manufacturing and/or patient identification data relative to a replacement lead of the pulse generator. When such information is stored in an electronic database, a clinician or manufacturer can quickly determine the current and historical configuration of the implantable medical device.

The identification module may also be a component of the communications module. The communications module can comprise any device capable of RF communication, including, but not limited to, an implantable medical device programmer. The communications module may also be adapted to communicate by other means. By way of non-limiting example only, such means may include electrical, acoustic or optical communication means.

The system may further be adapted to store values in a low-power implanted device, which would be read with a higher-powered second unit. For example, a low power pressure sensor or blood-contacting sensor makes a measurement and stores it in an active ID tag. A high-powered communications module could then read that data.

The medical device system may further comprise a component of an Advanced Patient Management ("APM") system. The APM system may be adapted to identify, monitor and analyze RFID data from a plurality of medical device systems and patients.

In a preferred embodiment, the medical device system is adapted to automatically and separately identify a plurality of medical device components in a plurality of patients. The RFID data includes manufacturing information about the particular component, such as the device's manufacturer, model number, lot number and serial number. By using an industry-wide standard for RFID data, like the ePC standard, the system can identify and monitor device components from a variety of manufacturers.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

GENERAL DESCRIPTION

Figure 1:
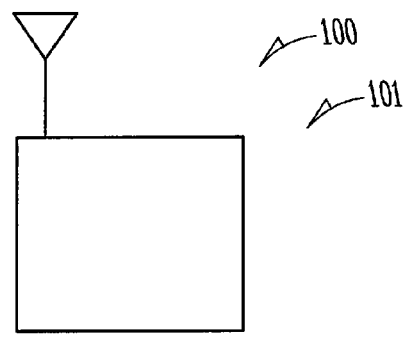
FIG. 1 is a diagram illustrating generally, among other things, the components of a radio frequency identification system.

By employing the use of electronic mechanisms for identification of model/serial number, manufacturing information and other summary information for IMD's and associated implantable medical device components such as atrial leads, ventricular leads or stents, the process of identifying and programming such devices can be simplified. In one embodiment, implantable medical devices and associated medical device components shall include an RFID chip, also referred to as an RFID tag, that would contain identification and in some embodiments summary information for each component of a patient health management system.

RFIDs are a generally inexpensive way to label products and provide a range of up to 100 feet, although 50 feet is typical. For read/write RFIDS, power can be generated from a variety of sources including the power supply of the implantable medial device. RFIDs typically employ the Electronic Product Code (EPC) standard.

RF tagging of medical devices would also allow the manufacturer to track the device during the manufacturing process and embed specific manufacturing data in the device. Tagging can also be used to store other information about the patient, such as the patient's medical history, clinician information and other medical data.

A system that is adapted to receive information transmitted from an RFID tag could access such identification and summary information about each device from the associated RFID tag and present such information to a clinician or even to the patient. The type of information and the amount of information stored on an RFID chip is determined by the type of RFID chip being used. RFID chips/tags are categorized as either active or passive. Active RFID tags are powered by an internal battery and are typically read/write, i.e., tag data can be rewritten and/or modified in the memory of a tag. An active tag's memory size varies according to application requirements. An active tag generally has enough data storage for storage of manufacturing information and other summary information. The battery-supplied power of an active tag generally gives it a longer read range. The tradeoff is greater size, greater cost, and an operational life limited to about 10 years, depending on operating temperatures and battery type. However, such an operational lifespan is well suited for an active tag included with an implantable medical device.

Passive RFID tags operate without an internal power source and obtain operating power that is generated by the device configured to read the tag data storage. Consequently, passive tags are much lighter than active tags, less expensive, and offer a virtually unlimited operational lifetime. The trade off is that they have shorter read ranges than active tags and require a higher-powered reader. Passive tags are typically read only and are programmed with a unique set of data (usually 32 to 128 bits) that cannot be modified.

In one embodiment, passive RFID tags may be used in the implantable components associated with an IMD, as well as in the IMD. In this embodiment, to retrieve the information from the RFID tag, an external instrument sends an excitation signal to each RFID tag associated with a device. The external instrument may be a controller, repeater or some other instrument capable of transmitting a broadcast message and reading the information stored on each tag. In an alternative embodiment, passive RFID tags may be used in the implantable components associated with an IMD and an active RFID tag may be used in the IMD. The battery within the IMD may control both the active and passive tags via electrical connections. Alternatively, utilizing this implantable configuration, an external instrument may be used to activate the passive and active RFID chips. In another alternative embodiment, utilizing this configuration, the external device may transmit a message to awaken the IMD tag read functions, which provide for reading of the IMD RFID tag and the RFID tags associated with the implantable components. It is also contemplated that the IMD RFID tag along with the passive tags of the associated implantable components may be activated at programmed intervals by the IMD. The IMD could retrieve and store data from the associated implantable component RFID tags and transmit such data to the external device.

Generally, the excitation signal energizes the RFID tag, and the RFID circuitry transmits the stored information back to the reader. The "reader" receives and decodes the information from the RFID tag. In view of the configuration of active RFID tags, such tags can retain and transmit enough information to uniquely identify individuals, associated device(s) and other summary data. RFID tags can also be used to store information that is written onto the RFID chip during process, such as system information and logistical histories.

In an embodiment in which the IMD provides for activation of all or selected RFID tags, the IMD includes a communications module that can communicates with the IMD RFID tag and the RFID tags associated with the implanted components. The communication between the RFID tags and the IMD allows the active system configuration to be quickly and accurately determined. This may be especially useful in the case where patients have had leads or other IMD components revised and an old lead or IMD component is still implanted. When the IMD and its associated components are identified, through the smarts of the clinician, and now through the smarts of the processor within the IMD or an external device, this information would provide a method for determining how the IMD and the associated components function together and what the characteristics of each component are.

It is also contemplated that in any embodiment in which an external device reads the RFID tags within an active system configuration, the identification module, which, depending on the embodiment, may be within the IMD or external device, knows the device capabilities within the system implanted within a patient. This knowledge, which may be read by a processor within the IMD or the external device processor, allows for the automatic configuration of active system components, which may thereby improve system performance. For example, if the external device determines, based on data received from the IMD regarding patient responsiveness to therapy that the IMD and or other components need to be reprogrammed, the external device may automatically reprogram the IMD and the other components in accordance with its knowledge of the full range of the capabilities of the IMD and the associated implanted components. In the above example, the patient may have a specific lead that has some enhanced capabilities. The external device programmer may reprogram the IMD allowing for the use of the full range of capabilities of the lead based on the external device's knowledge of the specifics of the lead, thereby enabling the lead and IMD to operate more effectively together.

Another use for RFID tags is in a manner that allows an external device to automatically identify the patient that is using a device associated with a patient management system. For example, external sensors such as weight scales, blood pressure monitors, and other patient initiated devices are being used in homes to track the health of patients. One factor that limits the usefulness of this data is the frequent occurrence that someone else uses the device. An RFID tag in a device implanted in the patient would allow positive identification of the user of the external sensor, which would allow a patient management system to accurately reject measurements that are not associated with the correct patient. In such an environment, the RFID tag within the IMD is an active tag that includes patient identification data that may be transmitted to the external sensor, which upon identification of the patient would store data associated with patient use of the external sensor. It is contemplated that there may be alternative configurations of the present invention that provide for patient identification and storage of data resulting from patient use of external sensors. The important aspect of these invention functions is that the configuration allows for recordation of external sensor data upon identification of the correct patient using the external sensor.

RF tags for IMDs, as used in the present invention, include patient identification and medical history data. Once the patient has been identified, the patient's medical record, if stored electronically in a patient management system or within the IMD for example, can be accessed quickly and efficiently by the clinician. An electronic patient record can also be easily transmitted and updated by the clinician, which allows the clinician to remotely monitor and assess the condition of the patient and the IMD and reduce or minimize the need for office or hospital visits. By integrating RFID and other identification technologies with computer database technology, populations of patients and IMDs can be easily monitored and compared, thereby providing the clinician with comprehensive information to assess and diagnose patient health within the context of a group of patients.

By coupling a reliable personal identification system to medical record access, including information on the patient's medical devices, an authorized person will have virtually unfettered access to critical medical data. Indeed, because a patient's medical information can be transmitted electronically; there are few limits on a clinician's ability to obtain medical information at any place or any time. In addition, once a proper personal identification has been made, a clinician, through a communications module including an interactive programmer, will be able to diagnose or reprogram an interactive implantable medical device, like a pulse generator or pacemaker.

Detailed Description

In the following detailed description, reference is made to the accompanying drawings that form a part hereof, and in which are shown by way of illustration specific embodiments or examples. These embodiments may be combined, other embodiments may be utilized, and structural, logical and electrical changes may be made without departing from the spirit and scope of the present invention. The following detailed description is, therefore, not to be taken in a limiting sense, and the scope of the present invention is defined by the appended claims and their equivalents.

The present system is described with respect to a system adapted to provide for radio frequency identification and tagging of implantable medical devices and components of such devices for the automatic identification of the devices and/or components and the patients using them. The system may further be adapted to communicate with external devices like an IMD programmer, a patient management system, a publicly available health kiosk, a weight scale, a blood pressure monitor, blood glucose monitor or other similar devices or systems. Such ubiquitous access to device and/or patient information allows the system to augment a health care regimen with current information on the function or type of a device and the status of a patient's health. In the embodiment described herein, the mechanism used to identify and tag IMDs and operatively associate and connect components is radio frequency (RF).

Figure 2:
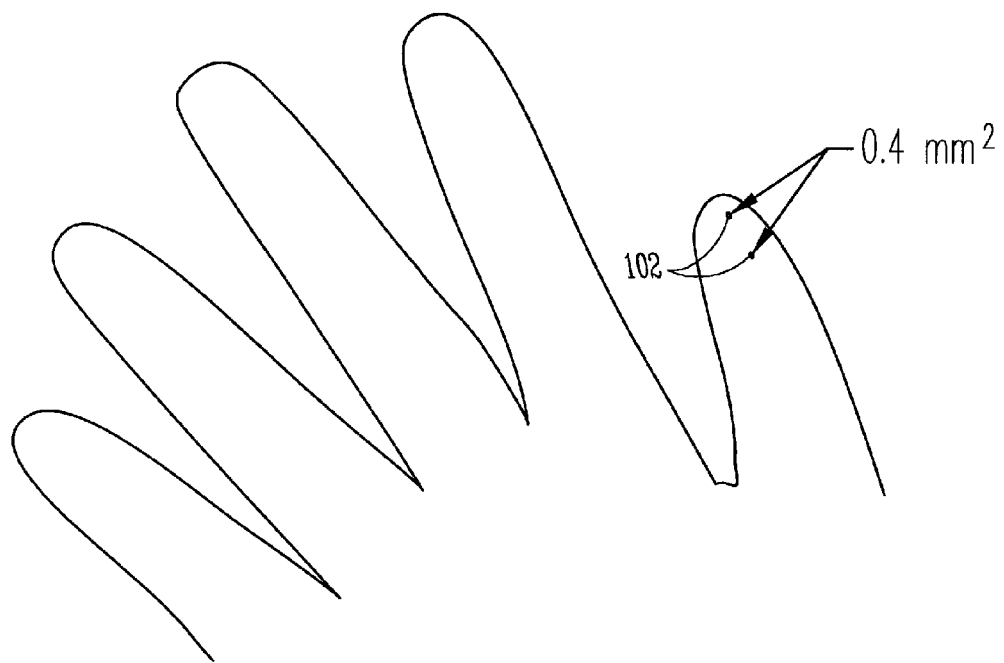
FIG. 2 is an illustration of the size of chip.

FIG. 1 is a diagram illustrating generally, among other things, the components of an identification system 100 utilizing radio frequency as the mechanism for tagging and identifying component parts of a implanted medical device system. Typically, such a system includes an external device 101 that may be adapted with a decoder (not shown) to read a RFID tagged device. External device 101 may be a transceiver, programmer, repeater or any other device capable of transmitting a broadcast message and receiving signals from implanted medical devices and other implanted components each having associated RFID tags that transmit signals responsive to a broadcast message or an activation signal. The external device 101 includes a communications module that controls transmission of broadcast messages and activation signals transmitted to the implanted RFID tags. The communications module also controls reception of signals received from the activated RFID tags that transmit signals. In response to the signals received from the RFID tags associated with the implanted medical devices and other implanted components, the external device 101, in some embodiments via the communications module, has the programming capability to determine which device of the implanted medical device system that it would like to communicate with from signals received from the RFID tags responding to the broadcast message. As shown in FIG. 2, the RFID tag 102 can be miniscule, comprising an area of about 0.4 mm$^2$. At this size, the RFID tag 102 is suitable for use with an implantable medical device or its component parts.

Figure 3:
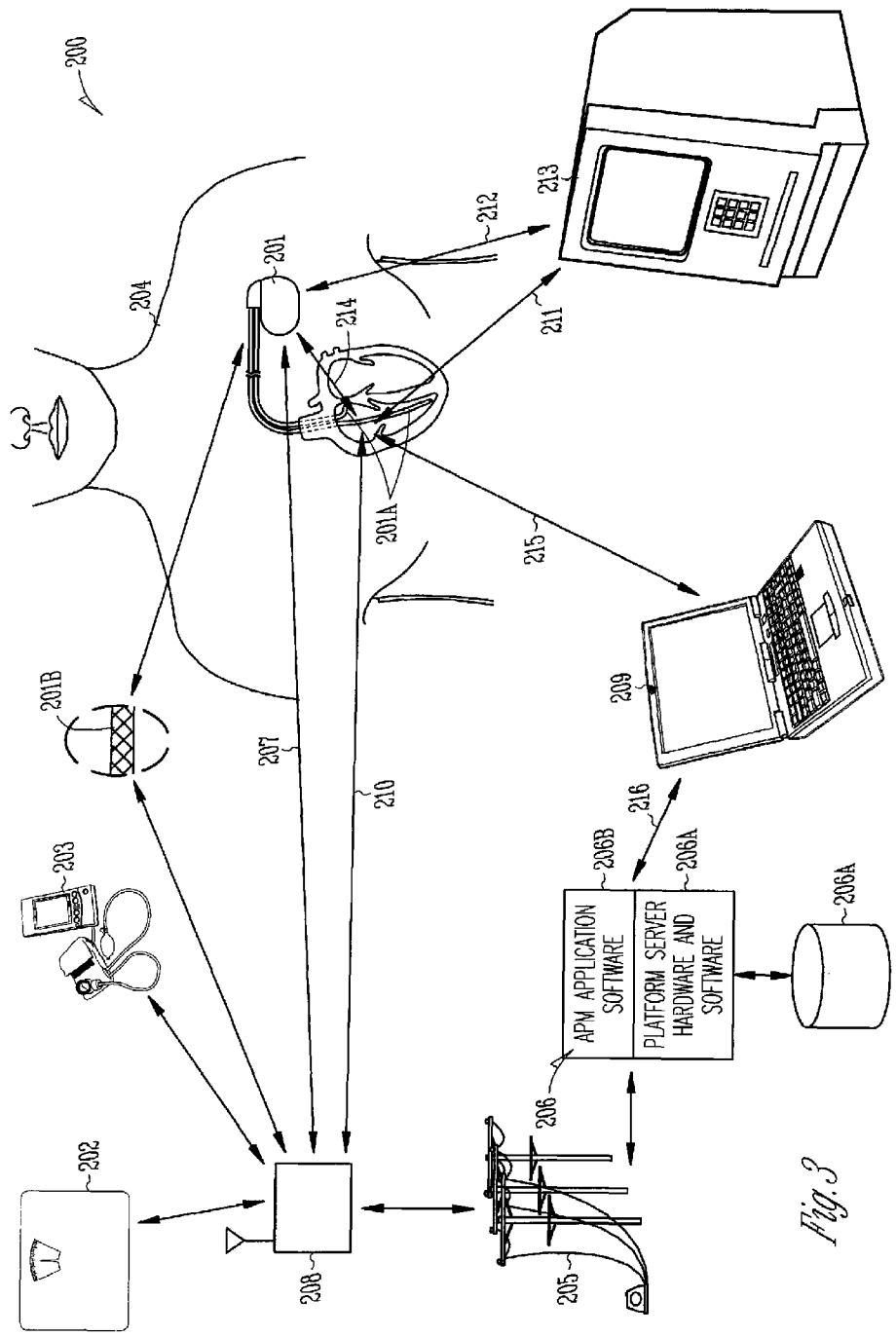
FIG. 3 is a diagram illustrating generally, among other things, one embodiment of a system for radio frequency identification and tagging of implantable medical device components and external devices, and the identification of a patient using such components and devices.

FIG. 3 is a diagram illustrating generally, among other things, one embodiment of a system 200 for radio frequency identification and tagging of implantable medical device components 201 and external devices 202 203 and the identification of a patient 204 using such components and devices. The system comprises an RFID tagged implantable medical device, like a pulse generator 201, adapted to sense and transmit patient health data, and a plurality of RFID tagged components, some of which are implanted and some of which are external. In the embodiment illustrated in FIG. 3, the external devices include a weight scale 202 and a blood pressure monitor 203, or other similar devices, such as a blood glucose monitor It is contemplated that the external devices may also include devices such as a publicly available health kiosk 213, which may also act as an external device, or other similar devices or systems adapted to communicate with an RFID tag and provide useful information concerning patient health or current device status such battery longevity, recall or upgrade information. The system shown in FIG. 3 further includes an external device in the form of a RFID tag reader or programmer 208 adapted to communicate with and identify RFID tagged devices. The system is also configured to transmit 205 RFID information. In the embodiment illustrated in FIG. 3, the system configuration 205 for transmitting RFID information is a traditional landline telephone system. It is also contemplated that the system configuration for transmitting an RFID signal may be via a wide area network and also via wireless telephony. The system further includes a patient management system 206 adapted to store and analyze RFID and patient health data. System components may be integrated for plug-and-play like compatibility. As further shown in FIG. 3, the system transceiver may be a component of the IMD 201, whereby the IMD itself is adapted to communicate with an RFID tagged component like, by way non-limiting example only, a lead 201a or stent 201b.

As also shown in FIG. 3, the implanted medical device 201 may comprise a device like a pacemaker or a defibrillator with various component parts, including leads 201a. The IMD may also comprise a device like a stent, including a coronary stent 201b. By way of non-limiting example only, IMDs suitable for use in the present disclosure may include pulse generators in general, pacemakers, implantable cardioverter defibrillators, neuro-devices, cardiac resynchronization devices, coronary stents, conventional stents, drug-eluting stents, mechanical or tissue heart valves, vascular grafts, peripheral grafts, endovascular grafts or arterial-to-venous (AV) grafts. Other implants or devices suitable for use in the present disclosure may include reconstructive orthopedic implants, knee implants, hip implants, shoulder implants, spinal implants, internal spinal fixation devices, spinal bone grafts and substitutes, bone substitutes, fusion cages, implantable spinal cord stimulators, fixation implants, internal fixation devices, bone grafts and substitutes, craniomaxillofacial implants, tissue implants, ophthalmic implants, intraocular lenses, retinal and other ophthalmic implants, cosmetic implants—breast implants, urological implants, penile implants, drug implants, drug inserts, radioactive seeds, implantable drug pumps, implantable neurological stimulators, cochlear implants and miscellaneous implants.

Other devices in various stages of research and development that may be suitable for use in the present disclosure as an implantable device include blood glucose monitors, blood chemistry sensors or monitors for tests such as BNP (b-type natriuretic peptide), arterial or blood pressure sensors, temperature sensors, pulse oximeters, heart rate sensors and respiration rate sensors, including minute ventilation sensors. By way of non-limiting example only, adapted external devices may include continuous positive airway pressure devices (CPAP), inductive plethysmography sensors, airflow sensors and impedance sensors.

The IMD and its components may include separate RFID tags, or if multiple IMDs are implanted within a patient 204, then each IMD and its component parts may include separate, unique RFID tags. By way of non-limiting example only, the RFID tag for an IMD may include model/serial number information, lot number information, other manufacturing information, patient information that specifically identifies the patient, or any other information that is or can be associated with either the device or the patient 204. The RFID tag for the leads or other components of the IMD 201 may also include the same or similar information as that for the IMD. Preferably, an IMD and its component parts, whether manufactured by the same manufacturer or not, utilize a standard RFID protocol. By way of non-limiting example only, the EPC standard is such a standard RFID protocol that is suitable for use in the present disclosure.

As further shown in FIG. 3, the implantable medical device 201, 201a, 201b may wirelessly transmit 207, 210 patient and component identification data to the external device 208. The external device may be a kiosk 213 where the implantable medical device 201, 201a, may wirelessly transmit 211, 212 patient and component identification data to the kiosk 213. Similiarly the implantable device 201 may wirelessly transmit 214 RFID tag information from the leads 201a to the pacemaker 201. In the present embodiment, such identification data is RF data. However, it is contemplated that the present invention is not limited to RF data and encompasses any identification protocol capable of functioning in conjunction with IMDs and implantable components operatively communicating with the IMD and external medical device components, including a programmer or any other advance patient management system components. Wired or wireless data transmission technologies may be employed for communication between the external device 208, or other devices 202, 203, 213. By way of non-limiting example only, wireless communication technologies may include radio, acoustic and optical technologies and be implemented via a communications module that may be further adapted for proximity recognition of the implantable medical device 201, 201a, 201b.

In the embodiment illustrated in FIG. 3, the external devices 202, 203 may comprise external sensors adapted to wirelessly communicate with an RF tagged device. Embodiments of suitable external sensors may include a RFID antenna, a publicly available kiosk, an implantable medical device programmer, a weight scale or a blood pressure monitor. Communicative external devices or sensors may also include a home interface system 209, like a desktop or portable personal computer, which may be used to present RFID information and analysis 216 or wirelessly transmit 215 patient and component identification data from the implantable device lead 201a. The devices or sensors 202 203 may include at least one antenna and/or at least one transceiver that is adapted to automatically activate when brought within operational range of an RF tagged device. In an embodiment where the external sensor includes a transceiver, the external sensor essentially functions as an implantable medical device reader, interrogator or programmer 208. In accordance with other embodiments of the system, the transceiver may also comprise a personal computing device. The reader or programmer 208 is adapted to transmit 205 RFID and other information to and from a database system, like an Advanced Patient Management ("APM") system 206.

APM is a system that helps patients, their physicians and their families to better monitor, predict and manage chronic diseases. In the embodiment shown in FIG. 2, the APM system 206 comprises three primary components: 1) an implantable medical device 201 with sensors adapted to monitor patient data, 2) a Data Management System ("DMS"), which is shown in this embodiment as Platform Server Hardware and Software 206a with storage capability and 3) an analytical component, which is shown in this embodiment as APM Application Software 206b that is adapted to analyze and correlate data from the DMS. APM is designed to support physicians and other clinicians in using a variety of different devices, patient-specific and non-specific data, along with medication therapy, to provide the best possible care to patients. The analytical component 206b of APM may include the use of clinically derived algorithms that reflect or embody a standard of medical care. Such standards of medical care can reflect the institutional practices and methodologies of institutions like, by way of non-limiting example only, the Cleveland Clinic, the Mayo Clinic or the Kaiser Permanente system, that have been reduced to algorithmic expression. Currently, implanted devices often provide only limited sensing, analysis and therapy to patients. APM moves the device from a reactive mode into a predictive one that allows a clinician to use APM to predict patient health.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including," "includes" and "in which" are used as the plain-English equivalents of the respective terms "comprising," "comprises" and "wherein."

What is claimed is:

1. A medical device system comprising a plurality of implantable components, including:
a plurality of radio frequency identification tags, wherein each of said tags is attached to or included with one of the plurality of implantable components and includes information specific to said one of the plurality of implantable components which said tag is attached to or included with, at least one of the plurality of radio frequency identification tags being powered by a power source of at least one of the plurality of implantable components, the power source powering at least one of the radio frequency identification tags and powering at least one of the plurality of implantable components other than the radio frequency identification tag;
a communications module, operatively connected to each identification tag, adapted to transmit an activation signal to each of said tags; and
an identification module, operatively connected to said communications module, adapted to automatically identify each of the plurality of radio frequency identification tags.

2. The medical device system of claim 1, wherein said information specific to a plurality of implantable components of the system includes manufacturing information.

3. The medical device system of claim 1, wherein said information specific to a plurality of implantable components of the system includes associated tagging information.

4. The medical device system of claim 1, wherein said identification tags further include information associated with a patient.

5. The medical device system of claim 1, further including an external medical device.

6. The medical device system of claim 1, wherein at least one of the plurality of implantable components comprises an internal sensor.

7. The medical device system of claim 1, wherein at least one of the plurality of implantable components includes the identification module.

8. The medical device system of claim 6, wherein at least one of the plurality of implantable components comprises a communications module.

9. The medical device system of claim 8, wherein at least one of the plurality of implantable components is adapted to communicate with at least another one of said plurality of implantable components comprising the medical device system.

10. The medical device system of claim 9, wherein the at least one of said plurality of implantable components comprises a stent.

11. The medical device of claim 9, wherein at least one of said plurality of implantable components comprises a lead.

12. The medical device system of claim 1, wherein the identification module is housed within a kiosk.

13. The medical device system of claim 1, wherein the communications module comprises an external sensor.

14. The medical device system of claim 1, wherein the system comprises a communicative network of sensors.

15. The medical device system of claim 1, wherein the medical device system comprises a component of an Advanced Patient Management including a plurality of medical data databases.

16. The medical device system of claim 15, wherein the plurality of medical data databases include patient data databases.

17. A medical device system comprised of a plurality of implantable medical device components, further comprising:
a plurality of radio frequency identification tags, wherein each of said plurality of tags is attached to or included with one of the plurality of implantable medical device components, and includes information specific to the associated implantable medical device component, at least one of the plurality of radio frequency identification tags being powered by a power source of at least one of the plurality of implantable medical device components, the power source powering at least one of the radio frequency identification tags and powering at least one of the plurality of implantable medical device components other than the radio frequency identification tag;
an identification module operatively communicating with the plurality of radio frequency identification tags and adapted to identify each of the plurality of radio frequency identification tags; and
a communications module operatively communicating with the identification module and adapted to communicate the identified plurality of radio frequency identification tags to a system processor operatively connected to the communications module.

18. A method, comprising:
tagging a plurality of implantable medical device components with unique radio frequency identification tags, at least one of the radio frequency identification tags being powered by a power source of at least one of the implantable components, the power source powering at least one of the radio frequency identification tags and powering at least one of the plurality of implantable components other than the radio frequency identification tag;
automatically identifying the radio frequency identification tags of the implantable components;
communicating the identified implantable components to a computer database; and
analyzing the identified implantable components.

19. The method of claim 18, wherein the step of tagging the implantable components with unique radio frequency identification tags includes tagging the implantable component with an RFID tag that identifies a patient.

20. The method of claim 19, wherein the step of tagging the implantable component with an RFID tag that identifies a patient includes identifying the patient.

21. The method of claim 18, wherein the step of communicating the identified implantable components to a computer database includes automatically engaging such communication when the implantable components come into operational proximity of the communications module.

22. The method of claim 18, wherein the step of analyzing the identified implantable components includes comparing the implantable components of a plurality of patients using an Advanced Patient Management system.

23. The method of claim 18, wherein the step of analyzing the identified implantable component includes analyzing a stored value in the implantable component.

24. A method, comprising:
tagging at least one of a plurality of implantable medical device components with a unique radio frequency identification tag, the radio frequency identification tag being powered by a power source of the at least one of the plurality of implantable components, the power source powering at least one of the radio frequency identification tags and powering at least one of the plurality of implantable components other than the radio frequency identification tag;
automatically identifying the radio frequency identification tags of each of the plurality of implantable components;
storing information in the radio frequency identification tag of the identified implantable component;
communicating the identified implantable component information to a computer database; and
analyzing the identified implantable components and the identified implantable component information.

* * * * *